United States Patent
Kennington

(10) Patent No.: US 11,520,775 B2
(45) Date of Patent: Dec. 6, 2022

(54) ADAPTIVE DATA SUB-SAMPLING AND COMPUTATION

(71) Applicant: Sartorius BioAnalytical Instruments, Inc., Bohemia, NY (US)

(72) Inventor: Aaron Kennington, Albuquerque, NM (US)

(73) Assignee: Sartorius BioAnalytical Instruments, Inc., Bohemia, NY (US)

(*) Notice: Subject to any disclaimer, the term of this patent is extended or adjusted under 35 U.S.C. 154(b) by 455 days.

(21) Appl. No.: 16/751,983

(22) Filed: Jan. 24, 2020

(65) Prior Publication Data

US 2021/0232569 A1 Jul. 29, 2021

(51) Int. Cl.
| | |
|---|---|
| *G06F 16/23* | (2019.01) |
| *G06F 16/2453* | (2019.01) |
| *G01N 15/14* | (2006.01) |
| *G01N 15/10* | (2006.01) |

(52) U.S. Cl.
CPC ..... *G06F 16/2379* (2019.01); *G01N 15/1429* (2013.01); *G06F 16/24549* (2019.01); *G01N 2015/1006* (2013.01)

(58) Field of Classification Search
CPC .......... G16H 40/63; G16H 10/40; G01N 2015/1402; G01N 15/14; G01N 15/1012; G01N 15/10; G01N 2015/1006; G01N 2015/1481; G01N 15/1459; G01N 15/1436; G01N 15/1434; G01N 15/1429; G06F 16/245; G06F 16/2453; G06F 16/24549; G06F 16/23; G06F 16/2379
See application file for complete search history.

(56) References Cited

U.S. PATENT DOCUMENTS

| | | | | |
|---|---|---|---|---|
| 9,964,968 | B2* | 5/2018 | Sharpe | G01N 15/1425 |
| 10,520,420 | B2* | 12/2019 | Smolak | G01N 15/1459 |
| 2010/0286963 | A1* | 11/2010 | Souloumiac | G06K 9/624 |
| | | | | 702/196 |

(Continued)

OTHER PUBLICATIONS

Zare et al., "Data reduction for spectral clustering to analyze high throughput flow cytometry data", BMC Bioinformatics, 2010, 11:403, pp. 1-16, http://www.biomedcentral.com/1471-2105/11/403.

(Continued)

*Primary Examiner* — John R Lee
(74) *Attorney, Agent, or Firm* — McDonnell Boehnen Hulbert & Berghoff LLP

(57) ABSTRACT

The multi-parameter data produced via flow cytometry and other biological analyses techniques can generate enormous amounts of data, which can take extensive time and/or computational resources to complete. Embodiments provided herein allow for adaptive sub-sampling of such data prior to analysis, allowing for such analyses to be performed while satisfying certain performance criteria. Such performance criteria may include, for example, keeping the latency of the analysis below a specified duration. This can allow analysis of data to be performed in real time as the data is generated, e.g., as flow cytometry data is generated by a cell counter or other flow cytometry instrument. This can also permit for data analyses to be iteratively developed or improved in less time by adaptively sub-sampling the data prior to re-analysis, so that the total time between iterations is reduced.

26 Claims, 6 Drawing Sheets

(56) References Cited

U.S. PATENT DOCUMENTS

| | | | | |
|---|---|---|---|---|
| 2012/0309636 | A1* | 12/2012 | Gibbons | G06T 3/4084 |
| | | | | 435/6.12 |
| 2016/0011083 | A1* | 1/2016 | Barnes | G01N 35/1011 |
| | | | | 356/246 |
| 2018/0247195 | A1* | 8/2018 | Kumar | G06N 3/08 |
| 2018/0247715 | A1* | 8/2018 | Kumar | G16H 15/00 |
| 2019/0127798 | A1* | 5/2019 | Hagstrom | G16B 40/20 |
| 2020/0232900 | A1* | 7/2020 | Gates | G01N 15/1429 |
| 2020/0294627 | A1* | 9/2020 | Lareau | G16B 40/00 |
| 2021/0073513 | A1* | 3/2021 | Porto | G06V 20/693 |
| 2021/0232569 | A1* | 7/2021 | Kennington | G06F 16/2379 |
| 2022/0082488 | A1* | 3/2022 | Jaimes | G01N 15/0205 |

OTHER PUBLICATIONS

Pyne et al., "Automated high-dimensional flow cytometric data analysis", PNAS, May 26, 2009, vol. 106, No. 21, pp. 8519-8524.

Van Gassen et al., "FlowSOM: Using Self-Organizing Maps for Visualization and Interpretation of Cytometry Data", Cytometry Part A, 87A: 636-645, 2015.

Linderman et al., "CytoSPADE: high-performance analysis and visualization of high-dimensional cytometry data", Bioinformatics Applications Note, vol. 28, No. 18, 2012, pp. 2400-2401, doi:10.1093/bioinformatics/bts425.

Flow Cytometry Data Preprocessing, GenePattern, https://www.genepattern.org/flow-cytometry-data-preprocessing, printed on Feb. 19, 2020.

Zaunders et al., "Computationally efficient multidimensional analysis of complex flow cytometry data using second order polynomial histograms: Analysis of Complex Flow Cytometry Data", International Society for Advancement of Cytometry, Cytometry Part A, 89A, vol. 9, No. 1, Jan. 1, 2016, pp. 44-58.

International Search Report and Written Opinion dated Apr. 26, 2021, issued in connection with International Patent Application No. PCT/US2021/012609, filed on Jan. 8, 2021.

\* cited by examiner

ADAPTIVE DATA SUB-SAMPLING AND COMPUTATION

BACKGROUND

A variety of biological experiments include the analysis of a great many samples, each of which may be associated with a number of parameters or other information generated via measurement or assessment of the sample. Such samples may include cells or other biological contents, each sample differing with respect to growth medium (e.g., hormones, cytokines, pharmaceuticals, or other substances in the growth medium), source (e.g., cultured, biopsied or otherwise explanted from natural tissue), incubation conditions (e.g., temperature, pH, light level or spectrum, ionizing radiation), exposure to viruses, bacteria, or other microorganisms, or some other controlled conditions in order to observe the response of the cells or other biological contents to the applied conditions. This could be done, e.g., in order to assess the response of the samples to a putative therapy, to elucidate some biological process, or to investigate some other question of interest.

Assessing such samples may include performing a variety of different investigations. In some examples, cells from the sample may be counted, identified, and/or sorted via flow cytometry. Additionally or alternatively, the samples may be imaged in order to assess morphology or other characteristics of the sample at one or more points in time. Imaging the whole sample can permit the sample to be assessed at multiple points in time without substantially disrupting the development of the sample. Fluorescent dyes or other substances may be added to the sample in order to facilitate such assessments (e.g., to permit analysis and/or visualization of proteins or other contents of interest within the samples, to identify or sort cells in the samples, etc.).

Performing an analysis on large, multi-parameter datasets such as those described above can be computationally costly. Accordingly, it can take an extended period of time to complete such an analysis. However, this extended time can be disadvantageous, especially where the analysis is re-calculated many times as part of an iterative development of the structure and parameters of the analysis. In such examples, it can be beneficial to reduce the size of the dataset (e.g., by eliminating data corresponding to sets of wells of a multi-well plate) in order to reduce the time needed to complete the analysis. However, existing methods for dataset reduction can often lead to analysis results that are not representative of the results of analysis of the non-reduced dataset.

SUMMARY

An aspect of the present disclosure relates to a method for adaptively sub-sampling flow cytometry data to reduce analysis computation time, the method including: (i) during a first period of time, receiving flow cytometry data, wherein the received flow cytometry data includes event data for a plurality of flow cytometry events; (ii) determining a data sub-sampling ratio based on a performance criterion; (iii) selecting, from the flow cytometry data, a sub-sample of the event data based on the sub-sampling ratio such that the selected sub-sample of the event data represents a portion of the flow cytometry events that corresponds to the data sub-sampling ratio; (iv) performing an analysis on the sub-sample of the event data, wherein determining the data sub-sampling ratio includes determining the data sub-sampling ratio such that performing the analysis on the sub-sample of the event data satisfies the performance criterion; and (v) providing an indication of a result of the analysis.

Another aspect of the present disclosure relates to a method for reducing flow cytometry data analysis computation time, the method including: (i) receiving, via a user interface, an indication of a data sub-sampling ratio; (ii) receiving flow cytometry data, wherein the received flow cytometry data includes event data for a plurality of flow cytometry events; (iii) selecting, from the flow cytometry data, a sub-sample of the event data based on the sub-sampling ratio such that the selected sub-sample of the event data represents a portion of the flow cytometry events that corresponds to the data sub-sampling ratio; (iv) performing a reduced analysis on the sub-sample of the event data; (v) providing, via the user interface, an indication of a result of the reduced analysis; (vi) receiving, via the user interface, an instruction to perform a full analysis; (vii) responsive to receiving the instruction to perform the full analysis, performing the full analysis on the flow cytometry data; and (viii) providing, via the user interface, an indication of a result of the full analysis.

Yet another aspect of the present disclosure relates to a method for adaptively sub-sampling multi-parameter data to reduce analysis computation time, the method including: (i) during a first period of time, receiving multi-parameter data, wherein the received multi-parameter data includes event data for a plurality of events; (ii) determining a data sub-sampling ratio based on a performance criterion; (iii) selecting, from the multi-parameter data, a sub-sample of the event data based on the sub-sampling ratio such that the selected sub-sample of the event data represents a portion of the events that corresponds to the data sub-sampling ratio; (iv) performing an analysis on the sub-sample of the event data, wherein determining the data sub-sampling ratio includes determining the data sub-sampling ratio such that performing the analysis on the sub-sample of the event data satisfies the performance criterion; and (v) providing an indication of a result of the analysis.

Yet another aspect of the present disclosure relates to a method for reducing multi-parameter data analysis computation time, the method including: (i) receiving, via a user interface, an indication of a data sub-sampling ratio; (ii) receiving multi-parameter data, wherein the received multi-parameter data includes event data for a plurality of events; (iii) selecting, from the multi-parameter data, a sub-sample of the event data based on the sub-sampling ratio such that the selected sub-sample of the event data represents a portion of the events that corresponds to the data sub-sampling ratio; (iv) performing a reduced analysis on the sub-sample of the event data; (v) providing, via the user interface, an indication of a result of the reduced analysis; (vi) receiving, via the user interface, an instruction to perform a full analysis; (vii) responsive to receiving the instruction to perform the full analysis, performing the full analysis on the multi-parameter data; and (viii) providing, via the user interface, an indication of a result of the full analysis.

Yet another aspect of the present disclosure relates to a computer-readable medium that is configured to store at least computer-readable instructions that, when executed by one or more processors of a computing device, cause the computing device to perform computer operations carrying out one or more of the methods described herein. Such a computer-readable medium could be a non-transitory computer-readable medium.

Yet another aspect of the present disclosure relates to a system including: (i) one or more processors; and (ii) a non-transitory computer-readable medium that is configured to store at least computer-readable instructions that, when executed by the one or more processors, cause the system to perform one or more of the methods described herein.

These as well as other aspects, advantages, and alternatives will become apparent to those of ordinary skill in the art by reading the following detailed description with reference where appropriate to the accompanying drawings. Further, it should be understood that the description provided in this summary section and elsewhere in this document is intended to illustrate the claimed subject matter by way of example and not by way of limitation.

DETAILED DESCRIPTION

Figure 1A:
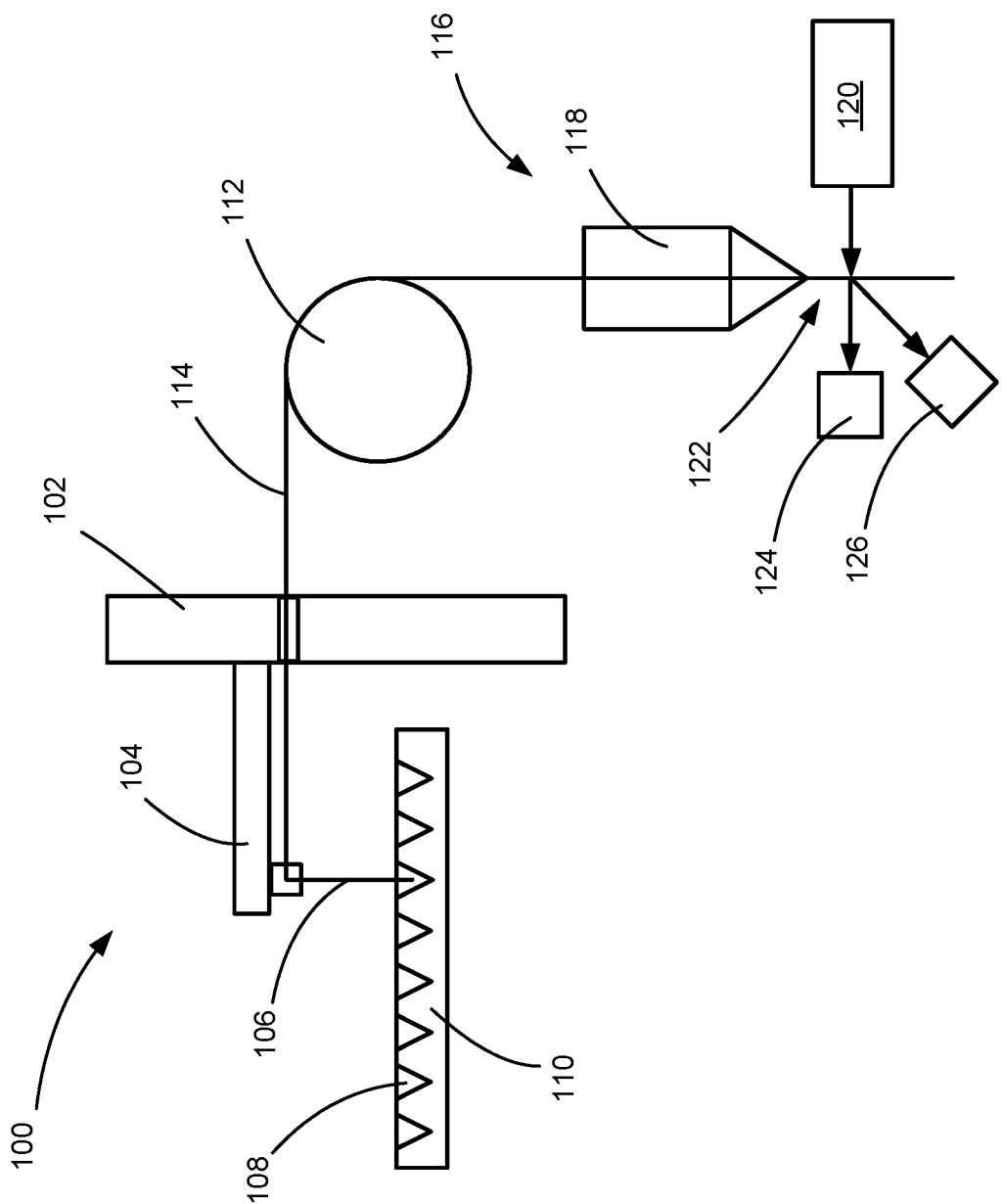
FIG. 1A is a schematic view of a flow cytometry apparatus.

Examples of methods and systems are described herein. It should be understood that the words "exemplary," "example," and "illustrative," are used herein to mean "serving as an example, instance, or illustration." Any embodiment or feature described herein as "exemplary," "example," or "illustrative," is not necessarily to be construed as preferred or advantageous over other embodiments or features. Further, the exemplary embodiments described herein are not meant to be limiting. It will be readily understood that certain aspects of the disclosed systems and methods can be arranged and combined in a wide variety of different configurations.

I. Overview

Experiments on biological systems can result in the generation of large amounts of multi-parameter data. For example, data may be generated for each of a large number of biological samples, with the data generated for each sample, itself, including a large number of parameters, images, events, or other information. Such an experiment could include dozens or hundreds of samples that vary with respect to growth medium, source, cell type, applied pharmaceuticals, or other factors and extensive data (e.g., fluorescent or other images, flow cytometry data), including a great many directly measured and/or derived parameters, could be generated for each of the samples. Accordingly, performing the data analysis for such experiments can be expensive with respect to time and/or computational resources.

In an example, flow cytometry could be performed to assess each sample of a set of samples (e.g., the contents of wells of a multi-well sample container). Cells or other particles could be taken from each sample and assessed by a flow cytometer to identify and count cells (or other particles) in the sample. The flow cytometer could output, for each detected cell/particle, multiple parameters related to forward- and/or side-scattered light, absorption, emission, and/or transmission of light at one or more wavelengths, or some other information related to each cell/particle detected from the sample. The multiple output parameters could include, for each detected cell/particle or other detected event, a pulse amplitude, width, shape, or other parameters related to each detected wavelength of light and/or to each wavelength of light used to illuminate the cells/particles (e.g., multiple wavelengths used to illuminate, and to detect light fluorescently emitted from, different fluorophores in the sample having respective different excitation and/or emission spectra). Such parameters could be directly detected as part of detecting an event (e.g., a detected intensity of light at a particular wavelength) or could be derived from such directly detected parameters (e.g., an emission peak determined from a plurality of detected light intensities, a predicted identity of the detected cell/particle, a ratio of one parameter to another parameter).

When specifying an analysis of such multi-parameter data, a user may select or de-select certain of the parameters (e.g., due to the sample lacking a fluorophore corresponding to the wavelength associated with a particular parameter, due to the particular parameter not appearing to vary with a factor of interest), leading to corresponding increases or decreases in the cost of computing the analysis.

The computational and time costs of analyzing multi-parameter data generated from an experiment (e.g., a flow cytometry experiment as described above) could have a variety of negative effects. For example, an analysis having too high a computational cost could render it difficult or impossible to provide the results of analysis of experimental data in real time as the data is generated (e.g., as samples of the experiment are imaged, assessed via flow cytometry, and/or assessed in some other manner). In some applications, a human user may iteratively develop the analysis by adjusting input parameters or other configuration data for the analysis in order to explore the data and/or improve the analysis prior to publication or some other use. In such examples, the analysis must be re-computed following such adjustments so that the human user can assess the effects of the adjustments and make further adjustments. However, such re-computation may take significant amounts of time, which can reduce the ability of the human user to intuit the effects of their adjustments or to devote sufficient time to fully develop the final analysis.

In some applications, it can be desirable to perform a reduced analysis, e.g., to perform an analysis on less than the entire dataset available or to perform an analysis that is otherwise reduced with respect to computational cost. For example, the analysis may be reduced in a manner that reduces the completeness or accuracy of the outputs of the analysis while also reducing the time and/or computational resources necessary to perform the analysis. Such a reduced analysis may be performed in order to provide a rough analysis of experimental data as it is generated by one or more instruments, e.g., to provide ongoing analysis in approximately "real time."

In another example, such a reduced analysis may be performed in order to provide a rough analysis of experimental data following user adjustments to the configuration and/or properties of the analysis (e.g., addition or subtraction of inputs to the analysis, addition or subtraction of particular analysis steps or types, adjustment of a p-value, learning rate, or other analysis parameter(s)). This could be done in order to provide feedback regarding the effect of the adjustments without requiring the full analysis to be reperformed each time. The time saved in such an example application by performing reduced analyses can be considerable, especially in examples where the user updates the analysis many times. Once the user has finished adjusting the analysis, the analysis can be performed in non-reduced fashion (a "full analysis") to provide results that may then be published or applied in some other manner.

Such a lower-cost reduced analysis could be performed by removing certain samples, parameters, or other aspects of the input data from the analysis. For example, where the data is generated from samples in different wells of a multi-well plate, the data from a set of the wells could be removed from the dataset in order to reduce the size of the dataset on which the analysis is performed. The cost in time and/or computational resources to perform such an analysis could then be reduced in proportion to the number of samples/parameters omitted from the analysis. However, an analysis reduced in this manner is also susceptible to being inaccurate in a manner that is biased. This could be due to its lacking the omitted samples and/or parameters. The output of such a reduced analysis could be particularly inaccurate where the omitted samples/parameters are particularly 'important' to the overall output of the analysis, e.g., in examples where the omitted samples and/or parameters exhibit behavior that departs significantly from the behavior of the non-omitted samples and/or parameters.

Instead, where the data includes a plurality of discrete 'events,' the event data can be sub-sampled to provide a reduced analysis of the data that is improved relative to omitting the data from whole samples or input parameters. For example, where the input data includes flow cytometry data, each detected cell or other particle could be such a discrete event. Accordingly, the analysis could be reduced with respect to computational time and/or cost by performing the analysis using only data from a subset of the events (e.g., data from a sub-sample of the cells or other particles detected via flow cytometry). By reducing the analysis in this manner, the output of the reduced analysis is less likely to be biased as a result of the sub-sampling of individual events than if the analysis was reduced by omitting whole samples, parameters, or other aspects of the input data. The output of an analysis reduced via event sub-sampling is thus likely to be more accurate relative to a non-reduced (or "full") analysis of the whole input dataset.

A multi-parameter dataset subject to an analysis as described herein may include a variety of discrete events that could be sub-sampled in order to reduce the cost of the analysis. As noted above, the dataset could include flow cytometry data, in which case the events could be individual detected cells, particles, or other flow cytometry events. Where the dataset includes a plurality of images of a sample (e.g., fluorescent images taken at regular intervals), each image could be an event, allowing for the images to be sub-sampled prior to analysis. Additionally or alternatively, individual cells or other contents of the samples represented in the images (e.g., cells, bacteria, or other contents identified via automated image segmentation techniques) could represent discrete events within the dataset that could be sub-sampled to reduce the cost of performing an analysis. This could include only performing the analysis on a subset of the cells identified within images of a sample, e.g., only determining, based on the image(s), a concentration or amount of a fluorophore contained within a subset of the cells represented in the image(s). In yet another example, the events could be particle detection events detected by a mass spectrometer, action potentials detected from the electrical of other activity of muscle or nervous cells in a sample, individual steps or other discrete elements of locomotion or other movement data, or some other discrete events that are present in and/or represented by a multi-parameter dataset.

Events represented in a multi-parameter dataset could be identified or otherwise detected during the generation of the dataset. For example, the dataset could include flow cytometry data and the events could be individual detected cells or other particles passing through a flow cell. Detection of a particle flowing through the flow cell could result in the generation of an amplitude, width, or other parameters related to forward-scattered light, side-scattered light, transmitted and/or fluorescently emitted light at one or more wavelengths, or some other parameters related to the particle detection event. Additionally or alternatively, events could be detected within the dataset following dataset generation. For example, events could include action potentials (detected electrophysiologically, via imaging of calcium-sensitive dyes, or by some other method) or other transient processes or behaviors observed in the dataset. Performing a reduced analysis on such a dataset could include identifying such events within the dataset, followed by performing additional analysis (e.g., statistics on the amplitude, width, timing or other parameters of the action potentials) only on a subset of the events identified within the dataset.

In order to perform an analysis on a sub-sampled portion of events in a multi-parameter dataset, a data sub-sampling ratio can be determined and the event data then sub-sampled according to the data sub-sampling ratio. For example, a sub-sampling ratio of 4:1 could be determined and used to select, from the available event data, a sub-sample that represents one quarter of the available event data.

Such a data sub-sampling ratio could be selected manually by a user, e.g., a user could select a data sub-sampling ratio of 2:1 in order to approximately halve the time taken to analyze a dataset while experiencing a corresponding reduction in the accuracy of the output of that reduced analysis. Alternatively, the data sub-sampling ratio could be determined adaptively in order to satisfy a performance criterion. For example, the data sub-sampling ratio could be specified such that the analysis can be performed, on a portion of events in the dataset that corresponds to the data sub-sampling ratio, in less than a specified duration of time. Such adaptive determination of the data sub-sampling ratio could be performed once (e.g., at the beginning of performance of a data analysis) or could be performed repeatedly. Repeated determination of the data sub-sampling ratio can allow the performance criterion to be satisfied even in the face of changes to the configuration of the analysis (e.g., addition or subtraction of parameters included in the analysis by a user), changes in the rate of generation of the data being analyzed in a real-time analysis scenario (e.g., an increase in detection rate of cells by a flow cytometer), changes in the operation of hardware used to perform the analysis (e.g., a failure of a hard drive of other component or an increase in data serving, internet streaming or communications, or other computational tasks that a server is performing in addition to performing an analysis), or changes in other factors that can affect the computation of an analysis of multi-parameter datasets as described herein.

Such a specified duration of time could, itself, be manually selected. For example, the specified duration could be selected according to a user's preference as regards waiting for the results of repeating the analysis following an adjustment of the specification of the analysis. Alternatively, the specified duration could be selected or determined such that the analysis can be updated repeatedly, based on data newly generated by a lab instrument, to give the appearance of having been updated in real time along with the newly generated data (e.g., the duration could be less than 100 milliseconds).

A data sub-sampling ratio could be determined in a variety of ways. In order to perform an analysis within a specified duration of time, the data sub-sampling ratio could be determined, based on the number of events in a dataset, such that the analysis takes less time to perform than the specified duration of time. In order to perform an analysis as a dataset is generated (e.g., in approximately real time such that the results of the analysis can be provided and updated as additional data is generated), the data sub-sampling ratio could be determined based on an average rate of generation or occurrence of the events such that the analysis takes less time to perform than the time it takes to generate the dataset (e.g., within a specified data capture period).

The data sub-sampling ratio could be determined based on an expected time and/or computational cost to perform the analysis, e.g., to perform some or all of the analysis for a single event within the event data. For example, the data sub-sampling ratio could be determined by dividing a goal duration of time by the number of events in the dataset and by a per-event computation cost. Such a computation cost could be determined for an analysis in a variety of ways. In some examples, the computation cost could be determined based on past performance(s) of an analysis and/or of portion(s) of the analysis. Additionally or alternatively, the computation cost could be determined based on a function or other algorithm operating on information about the analysis. For example, the computation cost could be determined using a function or algorithm that operates based on information about the number of input parameters to the analysis, an identity or other information about steps or sub-analyses of the analysis, or some other information that could be used to estimate the computational cost of performing the analysis. Such a function or other algorithm could include bias terms or other parameters that could be determined and/or updated based on past performance(s) of an analysis and/or of portion(s) of an analysis.

Determining the data sub-sampling ratio based on a performance metric (e.g., based on a specified duration during which the analysis should be completed) can allow the data sub-sampling ratio to be modified automatically to adapt to changes in the analysis (e.g., as parameters are added to or subtracted from the analysis as the analysis is iteratively developed), changes in the system used to perform the analysis (e.g., changes in available memory, in unrelated processes also being executed by the system), or other changes related to the performance of the analysis over time.

For example, a first data sub-sampling ratio could be determined for a first analysis (e.g., a first analysis that performs a first set of analytical tasks on a first selection of input parameters from a dataset) and used to select event data for a first subset of events represented in a dataset (e.g., a flow cytometry dataset). The first data sub-sampling ratio could be determined, based on particulars of the first analysis, such that the first analysis can be performed on the first subset of events according to a performance criterion (e.g., in less than a specified duration of time). An update to the first analysis could be received to define a second analysis. For example, a human user could add or subtract one or more available input parameters to the analysis. A second data sub-sampling ratio could then be determined, based on particulars of the second analysis, and used to select a second subset of events represented in the dataset such that the second analysis can be performed on the event data for the second subset of events according to a performance criterion (which may be the same or different from the performance criterion used to determine the first data sub-sampling ratio). Accordingly, the data sub-sampling ratio used to perform the analyses may be adapted over time such that the apparent performance of the analyses, from the perspective of a human user updating the analyses, remains substantially the same and/or varies by less than a specified amount.

If the performance criterion includes analyzing newly generated data as it is generated, the data sub-sampling ratio could be updated over time based on whether the updated analysis is being completed at the same time rate as the newly generated data is being generated. If the analysis is falling behind, the data sub-sampling ratio could be increased, so as to reduce the number of events that are being analyzed per unit time. Conversely, if the analysis is completing more quickly, the data sub-sampling ratio could be decreased, so as to increase the portion of the newly-generated events that are included in the analysis while still providing the updated analysis in effectively real time.

Once a data sub-sampling ratio has been determined, data corresponding to a corresponding proportion of events in a dataset (e.g., a dataset containing a plurality of flow cytometry events) can be selected and analyzed. This selection could be performed in a variety of ways. In some examples, the events could be selected randomly. This could include operating a random number generator or other hardware source of randomness to select which events to analyze. Alternatively, events can be randomly selected using a pre-generated pseudo-random sequence and/or the output of a pseudo-random number generator to select which events to analyze.

Alternatively, the events could be selected according to a pre-determined pattern. For example, if the data sub-sampling ratio is 4:1, then every fourth event in the dataset could be selected for analysis (with the other three in every four events omitted from the analysis). In another example, the data sub-sampling ratio is 4:1 and every first and second event out of eight in the dataset could be selected for analysis (with the other third through eighth event in every eight events omitted from the analysis).

The event data selected according to the data sub-sampling ratio could be selected from the set of all events available in the dataset. Alternatively, the events could be selected from a subset that has been pre-selected according to some criterion or other process. For example, a noise gate filter (or other type of filter) could be applied to all of the events in the dataset in order to determine which of the events are affected by noise by more than a threshold degree or that should be omitted from later analysis for some other reason (e.g., due to the event corresponding to a cell type that is outside the scope of the experiment). Applying such a noise gate filter could include determining a signal power, a signal to noise ratio, a maximum and/or minimum signal value, or some other parameter related to the presence and magnitude of noise present in the event data. Applying the noise gate filter could then include and determining, based on the determined parameter(s), whether to include the event data in later analysis or to omit/discard the event data. A data sub-sampling ratio could then be used to select a sub-sample of events that have already been selected according to the noise gate filter and/or according to some other pre-selection process.

A data analysis as described herein could be reduced in additional or alternative ways to sub-sampling the events as described above. As noted above, performing such a reduced analysis may allow the accuracy of the analysis to be traded for quicker performance or lowered computational cost of the analysis. This can be a beneficial trade when attempting to provide the analysis in real time as the source data is generated, when repeatedly re-computing the analysis while iteratively developing the analysis, or in other circumstances. Such alternative methods for reducing the computational cost of an analysis could be performed in addition to adaptive data sub-sampling or as an alternative to adaptive data sub-sampling. For example, a static data sub-sampling rate could be received from a user and used to sub-sample event data that is then applied to an analysis that is also reduced in one of the alternative analysis reduction methods described herein. Following performance of the reduced analysis one or more times (e.g., during iterative development of a finalized analysis configuration), the non-reduced analysis can be performed on the non-sub-sampled set of event data to generate an analysis output that can be published or applied in some other manner.

Such a reduced analysis may be reduced, relative to a non-reduced analysis, by omitting certain data pre-processing steps or sub-analyses. For example, the event data could include spectral information (e.g., about detected cells, particles, or other flow cytometry events) that may include cross-talk between different spectral channels. Such cross-talk could be due to overlaps between the excitation and/or emission spectra of different fluorophores (e.g., dyes introduced into a sample) that are present in a sample under test. In a non-reduced analysis, such cross-talk could be removed or reduced by applying spectral compensation to the spectra (e.g., based on observed levels of cross-talk between channels, mixing coefficients, etc.). A reduced analysis could omit such a spectral compensation step. Other varieties of compensation, normalization, or other pre-processing steps could be omitted when performing a reduced analysis relative to performance of a corresponding non-reduced analysis.

In another example, the non-reduced analysis could include performing a noisy data detection process to determine whether each event, sample, well, or other subsection of the multi-parameter dataset should be omitted from further processing. Such sample, well, or other subsection of the multi-parameter dataset could be omitted due to the omitted portion representing artifacts (e.g., air bubbles rather than cells or other particles of interest passing through a flow cytometer), out-of-bounds data, data that is irrelevant or otherwise not worth analyzing, wells or samples that have failed to incubate properly and/or that have been infected by outside agents, or due to some other factor or consideration. Such a noisy data detection process may be more computationally costly to perform than simply performing the remainder of a reduce analysis on all of the data (including those events or other aspects of the data that would have been omitted). Accordingly, a reduced analysis may omit such a noisy data detection process.

A reduced analysis may be reduced, relative to a non-reduced analysis, by omitting the determination of summary statistics for parameters of the data. Such summary statistics can be computationally expensive to determine (e.g., due to operating on the entire dataset, due to including sorts, multiply-and-accumulate, or other computationally expensive steps, or due to some other factor). A reduced analysis could omit determining a mean, a median, an average, a standard deviation, a third or higher-order cumulant, an entropy, a divergence, a fitted parametric distribution (e.g., a Gaussian, an exponential, a binomial, a logarithmic, a Poisson, or some other discrete or continuous distribution), or some other statistical information for a parameter determined from the event data as part of the reduced analysis. For example, a reduced analysis could include determining, for a particular parameter of the sub-sampled event data, bin boundaries for the parameter, counts of the parameter within each bin, and a histogram for the parameter. The corresponding non-reduced analysis could include these steps as well as determining a mean, a median, a standard deviation, and a fitted Gaussian distribution for the parameter.

A reduced analysis may be reduced, relative to a non-reduced analysis, by omitting the determination of certain complex analyses. For example, a reduced analysis could omit the determination of plate maps, heat maps, dose response curves, complex user-defined numerical calculations, the fitting of complex models to the dataset, and/or some other analyses. Additionally or alternatively, a reduced analysis may be reduced, relative to a non-reduced analysis, by performing certain analysis at a reduced level, e.g., at a reduced resolution. For example, a reduced analysis could generate histograms with fewer bins and/or with wider bins widths relative to histograms determined as part of a non-reduced (or "full") analysis. In another example, a reduced analysis could perform an iterative analysis process (e.g., gradient-descent fitting of parameters of a model to the dataset) using fewer iterations and/or until the changes in the model parameters or output accuracy change, from iteration to iteration, by less than a termination threshold value that is greater than a termination threshold value used to terminate the iterative analysis process when performed as part of a non-reduced analysis.

II. Example Systems

A variety of systems may be employed (e.g., programmed) to perform the various embodiments described herein. Such systems can include desktop computers, laptop computers, tablets, or other single-user workstations. Additionally or alternatively, the embodiments described herein may be performed by a server, cloud computing environment, or other multi-user system.

Such systems could analyze data received from other systems, e.g., data received from a remote data storage on a server, from a remote cell counter or other instrument, or from some other source. Additionally or alternatively, a system configured to perform the embodiments described herein may include and/or be coupled to an automated incubator, sample imaging system, cell sorter, flow cell, or other element of a flow cytometry apparatus, or some other instrument capable of generating experimental data for analysis. For example, such an instrument could include an incubator that contains a multi-well sample container. The samples within such a multi-well sample container could differ with respect to the genome of the samples, the source of the samples, the growth medium applied to the samples, a pharmaceutical, biologic, or microorganism applied to the samples, or some other condition applied to the samples.

Samples within such an apparatus could be experimentally assessed in a variety of ways. The samples could be imaged (e.g., using visible, infrared, and/or ultraviolet light). Such imaging could include fluorescent imaging of the contents of the samples, e.g., imaging fluorescent dyes or reporters added to the samples and/or generated by the cells of the samples (e.g., following insertion of genes coding for fluorophores). Additionally or alternatively, material (e.g., cells, growth medium) could be extracted from the samples for analysis via chromatography, mass spectrometry, cell counting or other flow cytometry methods, or analysis via some other method. An automated gantry could be located within such an incubator to facilitate imaging of the various samples within respective wells of the sample container, to facilitate cell counting or other flow cytometric analysis of the various samples within respective wells of the sample container (e.g., by maneuvering a suction tube or other apparatus configured to selectively extract cells or other contents from specified wells of the sample container), or to facilitate the measurement and analysis of the various samples within respective wells of the sample container.

FIG. 1A illustrates an exemplary flow cytometry apparatus 100 for use in connection with a well plate 110 or other variety of multi-well sample container. Flow cytometry apparatus 100 may be disposed wholly or partially within an incubator to facilitate control of the temperature or other environmental parameters applied to the samples in the multi-well sample container. Flow cytometry apparatus 100 includes an autosampler 102 having an adjustable arm 101 on which is mounted a hollow probe 106. As arm 104 moves back and forth (left and right in FIG. 1A) and side to side (into and out of the plane of FIG. 1A), probe 106 is lowered into individual source wells 108 of the well plate 110 to obtain a sample comprising particles (which may be tagged with a fluorescent tag (not shown in FIG. 1A)) to be analysed using flow cytometry apparatus 100. In between in-taking sample material from each of source wells 108, probe 106 may be operated to intake aliquots of a separation fluid (such as air), thereby forming a separation bubble between successive samples in the fluid flow stream.

Once a sample is picked up by probe 106, it is introduced into a fluid flow stream and a pump 112 (e.g., a peristaltic pump) forces the sample through a conduit 114 that extends from autosampler 102 through pump 112 and into a flow cytometer 116 including a flow cell 118 and a laser interrogation device 120. The flow cell 118 may be continuously operated to focus the fluid flow stream and to analyze the particles (e.g., cells) in each of the plurality of samples as the fluid flow stream passes through the flow cytometer. Laser interrogation device 120 examines individual samples flowing from flow cell 118 at a laser interrogation point 122.

Figure 1B:
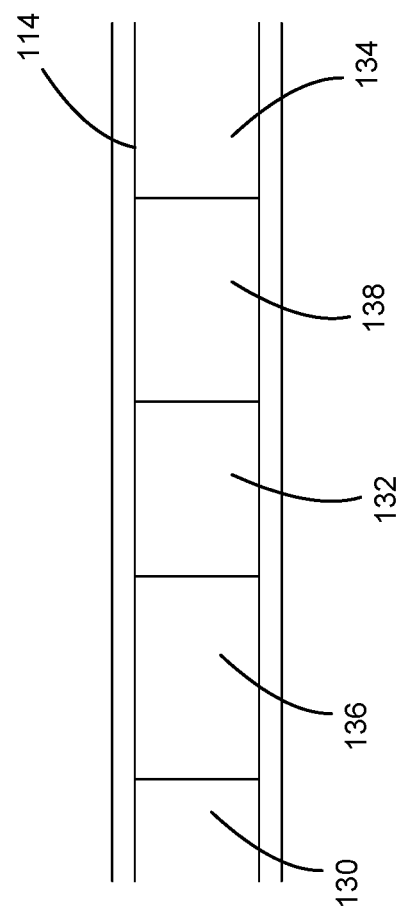
FIG. 1B is a cross-sectional schematic view of samples in a conduit of the flow cytometry apparatus of FIG. 1A.

FIG. 1B illustrates series of samples 130, 132 and 134 separated from each other by separation bubbles 136 and 138 in conduit 114, forming a bubble-separated fluid flow stream. In FIG. 1B, sample 130 is adjacent to sample 132, and sample 132 is adjacent to sample 134. When samples 130, 132 and 134 pass through laser interrogation point 122, the particles in the samples are sensed by flow cytometer 116. Forward scattered light is detected by a forward-scatter detector 124. Fluorescence emitted from tagged particles in the flow cell is detected by a fluorescence detector 126. Side scattered light may also be detected (e.g., by a side-scatter detector, not shown). In contrast, when air bubbles 136 and 138 pass through laser interrogation point 122, no particles are sensed. Therefore, a graph of the data points of fluorescence sensed versus time for a series of samples analysed using a flow cytometer will form distinct groups, each aligned with the time that a sample containing particles passes through the laser interrogation point. Such graphs can be generated by the output of both the forward scatter detector 124, the fluorescence detector 126, and/or other sensors entrained on the laser interrogation point 122.

Additionally or alternatively, an automated imaging system may be employed to obtain, in an automated fashion, images (e.g., fluorescence activity images) of a plurality of biological samples, in respective wells of a sample container, during a plurality of different scan periods over time. A set of images could be taken, by the automated imaging system, of each sample during each of the scan periods, e.g., a set of images taken at a rate of three images per second over a three minute scan period. The images can then be analyzed in order to determine some information about the samples, e.g., according to the methods described herein.

Use of such an automated imaging system can significantly reduce the personnel costs of imaging biological samples, as well as increasing the consistency, with respect to timing, positioning, and image parameters, of the images generated when compared to manual imaging. Further, such an automated imaging system can be configured to operate within an incubator, removing the need to remove the samples from an incubator for imaging. Accordingly, the growth environment for the samples can be maintained more consistently. Additionally, where the automated imaging system acts to move a microscope or other imaging apparatus relative to the sample containers (instead of, e.g., moving the sample container to be imaged by a static imaging apparatus), movement-related perturbation of the samples can be reduced. This can improve the growth and development of the samples and reduce movement-related confounds.

Such an automated imaging system can operate to obtain one or more images during scans that are separated by more than twenty-four hours, by more than three days, by more than thirty days, or by some longer period of time. The scans could be specified to occur at a specified rate, e.g., once per daily, more than daily, more than twice daily, or more than three times daily. The scans could be specified such that at least two, at least three, or some greater number of scans occurs within a twenty-four hour period. In some examples, data from one or more scans could be analyzed (e.g., according to the methods described herein) and used to determine the timing of additional scans (e.g., to increase a rate, duration, image capture rate, or some other property of the scans in order to detect the occurrence of a discrete event that is predicted to occur within a sample).

The use of such an automated imaging system can facilitate imaging of the same biological sample at multiple points in time over long time periods. Accordingly, the development and/or behavior of individual cells and/or networks of cells can be analyzed over time. For example, a set of cells, portions of cells, or other active objects could be identified, within a single sample, within scans taken during different, widely spaced periods of time. These sets of identified objects could then be compared between scans in order to identify the same active object(s) across the scans. Thus, the behavior of individual cells, or portions of cells, can be tracked and analyzed across hours, days, weeks, or months.

Figure 2:
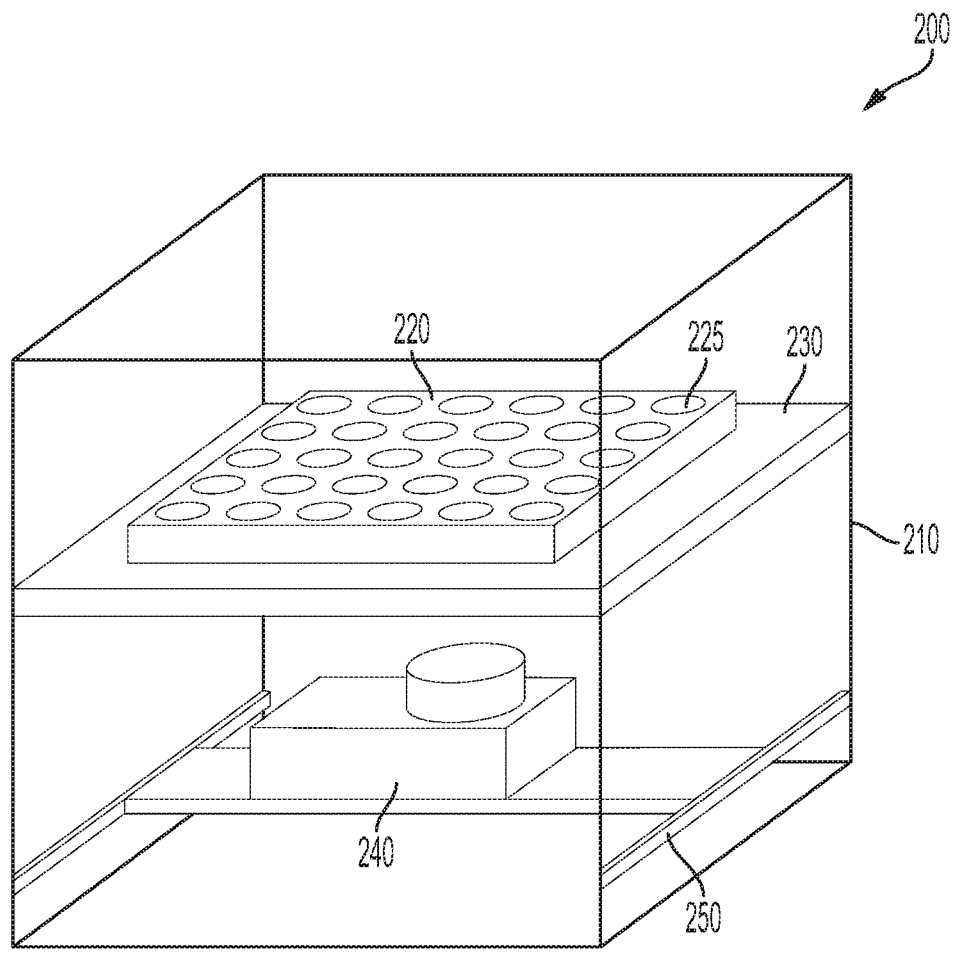
FIG. 2 depicts elements of an example automated sample imaging device.

FIG. 2 illustrates elements of such an automated imaging system 200. The automated imaging system 200 includes a frame 210 to which other elements of the automated imaging system 200 are attached. The frame 210 may be configured (e.g., sized) in order to fit within an incubator. The automated imaging system 200 includes a sample container 220 that is removably placed within a sample container tray 230 that is coupled to the frame 210. The sample container tray 230 could be removable and/or could include removable insert to facilitate holding a variety of different sample containers (e.g., a variety of industry-standard sample containers). The system 200 additionally includes an actuated gantry 250 configured to position an imaging apparatus 240 relative to the sample container 220 such that the imaging apparatus 240 can operate to obtain images of the contents of individual wells of the sample container 220 (e.g., the example well 225).

The imaging apparatus 240 can include a microscope, a fluorescence imager, a two-photon imaging system, a phase-contrast imaging system, one or more illumination sources, one or more optical filters, and/or other elements configured to facilitate imaging samples contained within the sample container 220. In some examples, the imaging apparatus 240 includes elements disposed on both sides of the sample container 220 (e.g., a source of coherent, polarized, monochromatic, or otherwise-specified illumination light in order to facilitate, e.g., phase contrast imaging of biological samples). In such examples, elements on both sides of the sample container 220 may be coupled to respective different gantries, to the same gantry, and/or elements on one side of the sample container 220 may not be movable relative to the sample container 220.

The actuated gantry 250 is coupled to the frame 210 and the imaging apparatus 240 and configured to control the location of the apparatus 240 in at least two directions, relative to the sample container 220, in order to facilitate imaging of a plurality of different samples within the sample container 220. The actuated gantry 250 may also be configured to control the location of the imaging apparatus 240 in a third direction, toward and away from the sample container 220, in order to facilitate controlling the focus of images obtained using the imaging apparatus 240 and/or to control a depth of material, within the sample container 220, that can be imaged using the imaging apparatus 240. Additionally or alternatively, the imaging apparatus 240 may include one or more actuators to control a focal distance of the imaging apparatus 240. The imaging apparatus 240 could include one or more motors, piezo elements, liquid lenses, or other actuators to facilitate controlling the focus setting of the imaging apparatus 240. For example, the imaging apparatus 240 could include an actuator configured to control a distance between the imaging apparatus 240 and a sample being imaged. This could be done in order to ensure that the image is taken in-focus and/or to allow images to be taken at a variety of different focus settings to facilitate the image correction methods.

The actuated gantry 250 may include elements configured to facilitate detection of the absolute and/or relative location of the imaging apparatus 240 relative to the sample container 220 (e.g., to particular well(s) of the sample container 220). For example, the actuated gantry 250 may include encoders, limit switches, and/or other location-sensing elements. Additionally or alternatively, the imaging apparatus 240 or other elements of the system may be configured to detect fiducial marks or other features of the sample container 220 and/or of the sample container tray 230 in order to determine the absolute and/or relative location of the imaging apparatus 240 relative to the sample container 220.

Computational functions (e.g., functions to operate the actuated gantry 250 and/or imaging apparatus 240 to image samples within the sample container 220 during specified periods of time, to operate the autosampler 102, flow cytometer 116, or other elements of the flow cytometry apparatus 100, and/or to perform some other method described herein) may be performed by one or more computing systems. Such a computing system may be integrated into a laboratory instrument system (e.g., 100, 200), may be associated with such a system (e.g., by being connected via a direct wired or wireless connection, via a local network, and/or via a secured connection over the internet), and/or may take some other form (e.g., a cloud computing system that is in communication with an automated imaging system and/or that has access to a store of images of biological samples).

Figure 3:
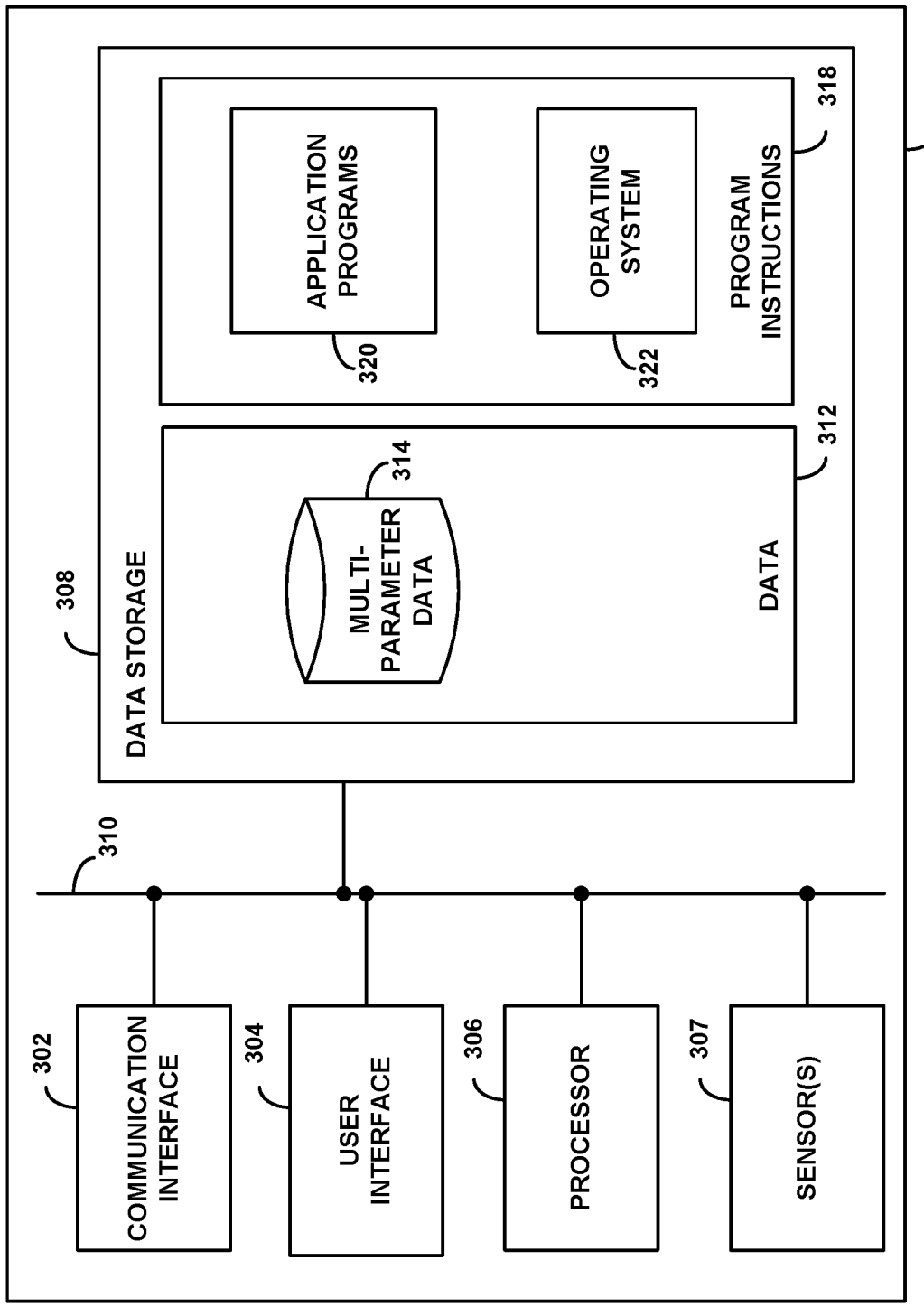
FIG. 3 depicts elements of an example system that may be used to implement the data sub-sampling methods described herein.

FIG. 3 illustrates an example of such a computing system 300, which may be used to implement the methods described herein. The example computing system 300 includes a communication interface 302, a user interface 304, a processor 306, one or more sensors 307 (e.g., photodetectors, cameras, or other sensors of a flow cytometry apparatus, a microscope, a mass spectrometer, or some other instrumented laboratory apparatus), and data storage 308, all of which are communicatively linked together by a system bus 310.

The communication interface 302 may function to allow the computing system 300 to communicate, using analog or digital modulation of electric, magnetic, electromagnetic, optical, or other signals, with other devices, access networks, and/or transport networks. Thus, communication interface may facilitate circuit-switched and/or packet-switched communication, such as plain old telephone service (POTS) communication and/or Internet protocol (IP) or other packetized communication. For instance, communication interface 302 may include a chipset and antenna arranged for wireless communication with a radio access network or an access point. Also, communication interface 302 may take the form of or include a wireline interface, such as an Ethernet, Universal Serial Bus (USB), or High-Definition Multimedia Interface (HDMI) port. Communication interface may also take the form of or include a wireless interface, such as a WiFi, BLUETOOTH®, global positioning system (GPS), or wide-area wireless interface (e.g., WiMAX or 3GPP Long-Term Evolution (LTE)). However, other forms of physical layer interfaces and other types of standard or proprietary communication protocols may be used over communication interface 302. Furthermore, communication interface 302 may comprise multiple physical communication interfaces (e.g., a WiFi interface, a BLUETOOTH® interface, and a wide-area wireless interface).

In some embodiments, the communication interface 302 may function to allow computing system 300 to communicate with other devices, remote servers, access networks, and/or transport networks. For example, the communication interface 302 may function to transmit and/or receive an indication of images of biological samples (e.g., fluorescence activity images), to transmit and/or receive an indication of flow cytometry information related to one or more biological samples, or some other information.

The user interface 304 of such a computing system 300 may function to allow computing system 300 to interact with a user, for example to receive input from and/or to provide output to the user. Thus, user interface 304 may include input components such as a keypad, keyboard, touch-sensitive or presence-sensitive panel, computer mouse, trackball, joystick, microphone, and so on. User interface 304 may also include one or more output components such as a display screen which, for example, may be combined with a presence-sensitive panel. The display screen may be based on CRT, LCD, and/or LED technologies, or other technologies now known or later developed. User interface 304 may also be configured to generate audible output(s), via a speaker, speaker jack, audio output port, audio output device, earphones, and/or other similar devices.

In some embodiments, user interface 304 may include a display that serves to present video or other images to a user (e.g., video of images generated during a particular scan of a particular biological sample). Additionally, user interface 304 may include one or more buttons, switches, knobs, and/or dials that facilitate the configuration and operation of the computing device. It may be possible that some or all of these buttons, switches, knobs, and/or dials are implemented as functions on a touch- or presence-sensitive panel. The user interface 304 may permit a user to specify the types of samples contained within an automated imaging system, to specify a schedule for imaging or other assessment of the samples, to specifying parameters of image segmentation, event analysis, and/or some other analysis to be performed by the system 300, or to input some other commands or parameters for operation of an automated laboratory system and/or for analysis of data generated thereby.

Processor 306 may comprise one or more general purpose processors—e.g., microprocessors—and/or one or more special purpose processors—e.g., digital signal processors (DSPs), graphics processing units (GPUs), floating point units (FPUs), network processors, tensor processing units (TPUs), or application-specific integrated circuits (ASICs). In some instances, special purpose processors may be capable of image processing, image alignment, statistical analysis, filtering, or noise reduction, among other applications or functions. Data storage 308 may include one or more volatile and/or non-volatile storage components, such as magnetic, optical, flash, or organic storage, and may be integrated in whole or in part with processor 306. Data storage 308 may include removable and/or non-removable components.

Processor 306 may be capable of executing program instructions 318 (e.g., compiled or non-compiled program logic and/or machine code) stored in data storage 308 to carry out the various functions described herein. Therefore, data storage 308 may include a non-transitory computer-readable medium, having stored thereon program instructions that, upon execution by computing device 300, cause computing device 300 to carry out any of the methods, processes, or functions disclosed in this specification and/or the accompanying drawings. The execution of program instructions 318 by processor 306 may result in processor 306 using data 312.

By way of example, program instructions 318 may include an operating system 322 (e.g., an operating system kernel, device driver(s), and/or other modules) and one or more application programs 320 (e.g., filtering functions, data processing functions, statistical analysis functions, image processing functions, event sub-sampling functions) installed on computing device 300. Data 312 may include flow cytometry data, microcopy images, or other multi-parameter data that includes information for a plurality of events (e.g., detected cells or other particles or other flow cytometry events).

Application programs 320 may communicate with operating system 322 through one or more application programming interfaces (APIs). These APIs may facilitate, for instance, application programs 320 receiving information via communication interface 302, receiving and/or displaying information on user interface 304, performing full or reduced analyses on events in the multi-parameter data 314 and/or on a sampled sub-set of the events therein, and so on.

Application programs 320 may take the form of "apps" that could be downloadable to computing device 300 through one or more online application stores or application markets (via, e.g., the communication interface 302). However, application programs can also be installed on computing device 300 in other ways, such as via a web browser or through a physical interface (e.g., a USB port) of the computing device 300.

In some examples, portions of the methods described herein could be performed by different devices, according to an application. For example, different devices of a system could have different amounts of computational resources (e.g., memory, processor cycles) and different information bandwidths for communication between the devices. For example, a first device could be an embedded processor(s) that could operate an actuated gantry, imaging apparatus, flow cytometry apparatus, or other elements to generate information about biological samples at and/or during a plurality of different periods. A second device could then receive (e.g., via the internet, via a dedicated wired link), from the first device, information (e.g., image information, flow cytometry data, and/or event information) from the first device and perform the processing and analysis methods described herein on the received data. Different portions of the methods described herein could be apportioned according to such considerations.

V. Example Methods

Figure 4:
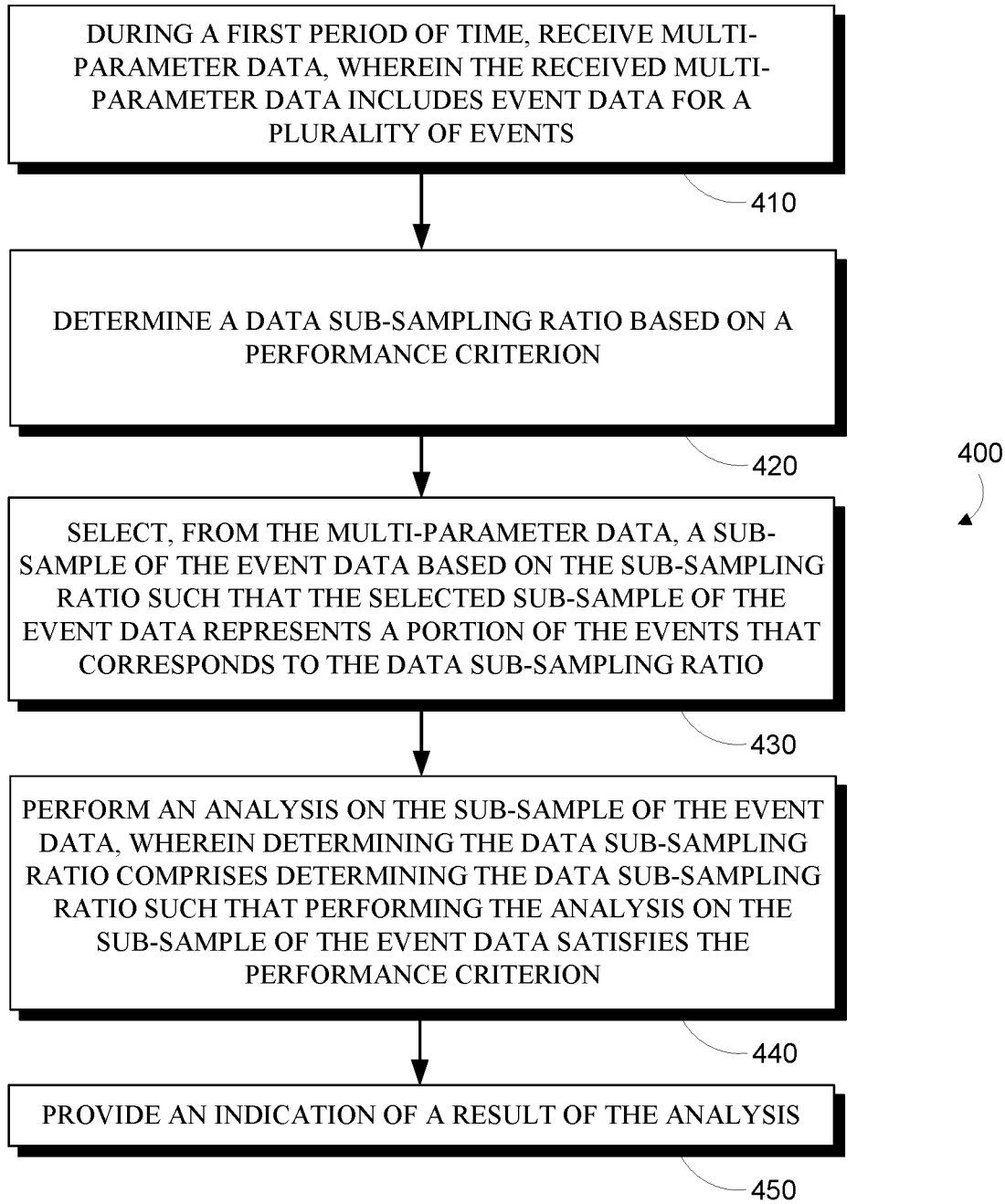
FIG. 4 is a flowchart of an example method for adaptively sub-sampling multi-parameter data.

FIG. 4 is a flowchart of a method 400 for adaptively sub-sampling multi-parameter data (e.g., flow cytometry data) to reduce analysis computation time. Such a method can be advantageous in circumstances where a reduced-accuracy analysis result is acceptable if that reduced accuracy result can be completed in less time, e.g., to enable effectively real-time analysis as the data is generated, or to reduce analysis time when iteratively specifying the contents and defining parameters of the analysis.

The method 400 includes, during a first period of time, receiving multi-parameter data, wherein the received multi-parameter data includes event data for a plurality of events (410). Such multi-parameter data can be flow cytometry data, in which case the events could be flow cytometry events (e.g., individual detected cells or other particles).

The method 400 additionally includes determining a data sub-sampling ratio based on a performance criterion (420). Such a performance criterion could be a real-time latency criterion, in which case determining the data sub-sampling ratio based on the performance criterion could include determining the data sub-sampling ratio based on an average rate of occurrence of the events such that such that the analysis takes less time to perform than a duration of the first period of time (e.g., such that the results of the analysis can be determined at or near realtime). Such a performance criterion could be an analysis duration criterion, in which case determining the data sub-sampling ratio based on the performance criterion could include determining the data sub-sampling ratio based on a number of the events in the multi-parameter data such that the analysis can be performed in less than a specified duration of time.

The method 400 additionally includes selecting, from the multi-parameter data, a sub-sample of the event data based on the sub-sampling ratio such that the selected sub-sample of the event data represents a portion of the events that corresponds to the data sub-sampling ratio (430). This could include selecting the events according to a pre-specified pattern (e.g., every other event for a 50% ratio, or some other regular pattern), or selecting the events randomly.

The method 400 further includes performing an analysis on the sub-sample of the event data, wherein determining the data sub-sampling ratio comprises determining the data sub-sampling ratio such that performing the analysis on the sub-sample of the event data satisfies the performance criterion (440).

The method 400 further includes providing an indication of a result of the analysis (450).

The method 400 could include additional elements or features.

Figure 5:
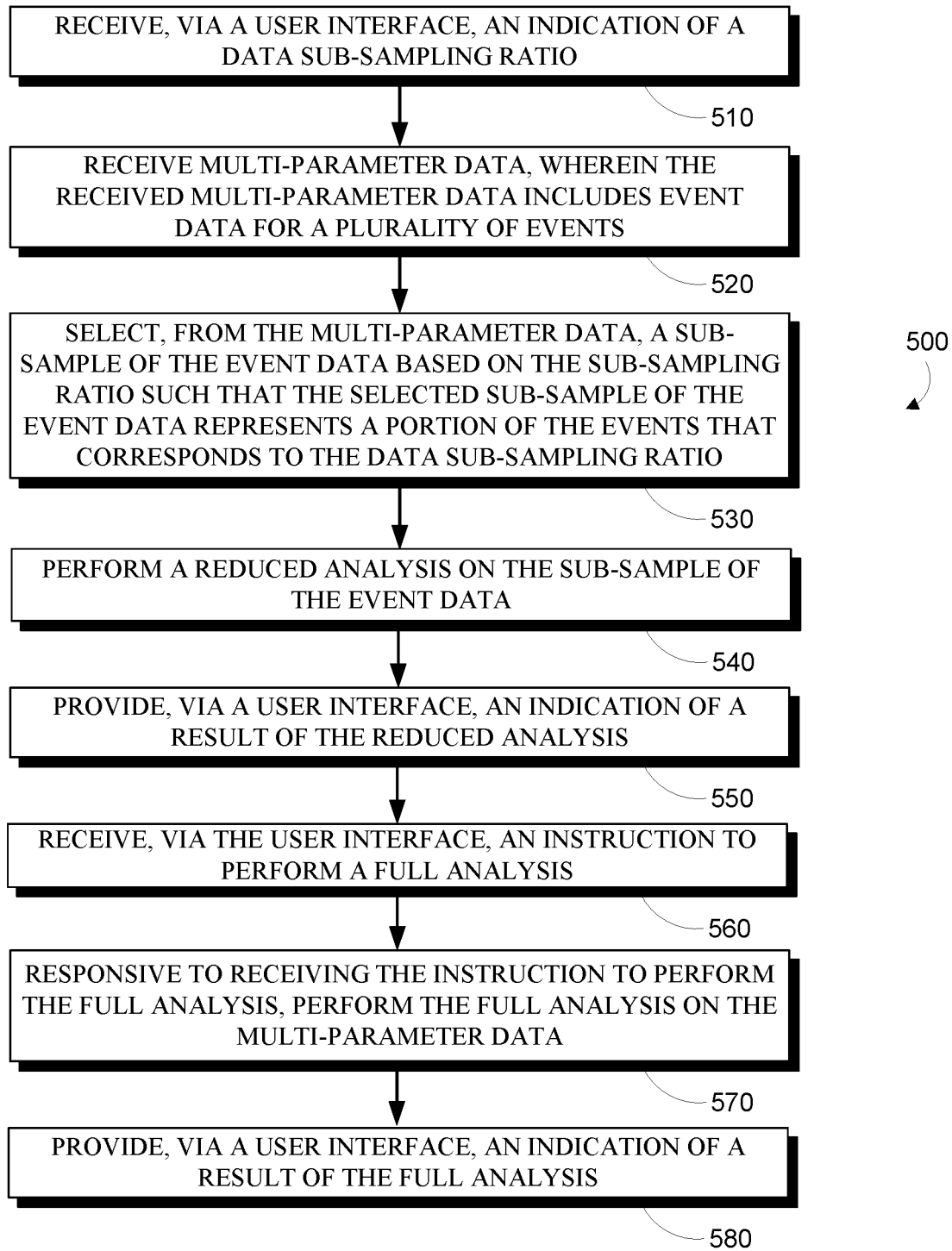
FIG. 5 is a flowchart of an example method for reducing multi-parameter data analysis computation time.

FIG. 5 is a flowchart of a method 500 for reducing multi-parameter data (e.g., flow cytometry data) analysis computation time. Such a method can be advantageous in circumstances where a reduced-accuracy analysis result is acceptable if that reduced accuracy result can be completed in less time, e.g., to enable effectively real-time analysis as the data is generated, or to reduce analysis time when iteratively specifying the contents and defining parameters of the analysis.

The method 500 includes receiving, via a user interface, an indication of a data sub-sampling ratio (510). The method 500 additionally includes receiving multi-parameter data, wherein the received multi-parameter data includes event data for a plurality of events (520). Such multi-parameter data can be flow cytometry data, in which case the events could be flow cytometry events (e.g., individual detected cells or other particles).

The method 500 additionally includes selecting, from the multi-parameter data, a sub-sample of the event data based on the sub-sampling ratio such that the selected sub-sample of the event data represents a portion of the events that corresponds to the data sub-sampling ratio (530). This could include selecting the events according to a pre-specified pattern (e.g., every other event for a 50% ratio, or some other regular pattern), or selecting the events randomly.

The method 500 further includes performing a reduced analysis on the sub-sample of the event data (540). Performing a reduced analysis can include performing an analysis that omits certain data preprocessing steps (e.g., noise removal or filtering steps, erroneous event detection and rejection steps), that omits the determination of certain sample statistics (e.g., mean, median, mode, or other summary statistics for samples of events within the data), that omits the determination of histograms and/or that includes the determination of histograms having reduced resolution and/or fewer bins relative to a non-reduced analysis, or that is reduced in some other manner relative to a non-reduced, or "full," analysis.

The method 500 further includes providing, via the user interface, an indication of a result of the reduced analysis (550).

The method 500 further includes receiving, via the user interface, an instruction to perform a full analysis (560).

The method 500 further includes, responsive to receiving the instruction to perform the full analysis, performing a full analysis on the multi-parameter data (570). Such a full analysis could be "full" in the sense that it is non-reduced relative to the reduced analysis. For example, performing the full analysis could include performing certain data preprocessing steps, determining certain sample statistics, determining histograms and/or determining histograms having increased resolution and/or more bins relative to a non-reduced analysis, or performing some other analysis that is omitted from the reduced analysis and/or performing some other analysis in a manner that is relatively more complex than a reduced version of the analysis that is performed as part of the reduced analysis.

The method 500 further includes providing, via the user interface, an indication of a result of the full analysis (580).

The method 500 could include additional elements or features.

VI. Conclusion

The above detailed description describes various features and functions of the disclosed systems, devices, and methods with reference to the accompanying figures. In the figures, similar symbols typically identify similar components, unless context indicates otherwise. The illustrative embodiments described in the detailed description, figures, and claims are not meant to be limiting. Other embodiments can be utilized, and other changes can be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the message flow diagrams, scenarios, and flowcharts in the figures and as discussed herein, each step, block and/or communication may represent a processing of information and/or a transmission of information in accordance with example embodiments. Alternative embodiments are included within the scope of these example embodiments. In these alternative embodiments, for example, functions described as steps, blocks, transmissions, communications, requests, responses, and/or messages may be executed out of order from that shown or discussed, including in substantially concurrent or in reverse order, depending on the functionality involved. Further, more or fewer steps, blocks and/or functions may be used with any of the message flow diagrams, scenarios, and flow charts discussed herein, and these message flow diagrams, scenarios, and flow charts may be combined with one another, in part or in whole.

A step or block that represents a processing of information may correspond to circuitry that can be configured to perform the specific logical functions of a herein-described method or technique. Alternatively or additionally, a step or block that represents a processing of information may correspond to a module, a segment, or a portion of program code (including related data). The program code may include one or more instructions executable by a processor for implementing specific logical functions or actions in the method or technique. The program code and/or related data may be stored on any type of computer-readable medium, such as a storage device, including a disk drive, a hard drive, or other storage media.

The computer-readable medium may also include non-transitory computer-readable media such as computer-readable media that stores data for short periods of time like register memory, processor cache, and/or random access memory (RAM). The computer-readable media may also include non-transitory computer-readable media that stores program code and/or data for longer periods of time, such as secondary or persistent long term storage, like read only memory (ROM), optical or magnetic disks, and/or compact-disc read only memory (CD-ROM), for example. The computer-readable media may also be any other volatile or non-volatile storage systems. A computer-readable medium may be considered a computer-readable storage medium, for example, or a tangible storage device.

Moreover, a step or block that represents one or more information transmissions may correspond to information transmissions between software and/or hardware modules in the same physical device. However, other information transmissions may be between software modules and/or hardware modules in different physical devices.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

I claim:

1. A method for sub-sampling flow cytometry data to reduce analysis computation time, the method comprising:
during a first period of time, receiving flow cytometry data, wherein the received flow cytometry data includes event data for a plurality of flow cytometry events;
determining a data sub-sampling ratio based on a performance criterion;
selecting, from the flow cytometry data, a sub-sample of the event data based on the sub-sampling ratio such that the selected sub-sample of the event data represents a portion of the flow cytometry events that corresponds to the data sub-sampling ratio;
performing an analysis on the sub-sample of the event data, wherein determining the data sub-sampling ratio comprises determining the data sub-sampling ratio such that performing the analysis on the sub-sample of the event data satisfies the performance criterion; and
providing an indication of a result of the analysis.

2. The method of claim 1, wherein performing the analysis and providing the indication of the result of the analysis are performed during the first period of time.

3. The method of claim 2, wherein the performance criterion is a real-time latency criterion, and wherein determining the data sub-sampling ratio based on the performance criterion comprises determining the data sub-sampling ratio based on an average rate of occurrence of the flow cytometry events such that such that the analysis takes less time to perform than a duration of the first period of time.

4. The method of claim 2, wherein performing the analysis on the sub-sample of the event data comprises updating the analysis a plurality of times during the first period of time as the flow cytometry data is received, and wherein providing the indication of the result of the analysis comprises providing an updated indication a plurality of times during the first period of time as the analysis is updated.

5. The method of claim 1, wherein the performance criterion is an analysis duration criterion, and wherein determining the data sub-sampling ratio based on the performance criterion comprises determining the data sub-sampling ratio based on a number of the flow cytometry events in the flow cytometry data such that the analysis can be performed in less than a specified duration of time.

6. The method of claim 5, wherein the analysis is characterized by a number of parameters, and wherein determining the data sub-sampling ratio further comprises determining an expected computation cost for the analysis based on the number of parameters.

7. The method of claim 1, further comprising:
selecting, from the flow cytometry data, a de-noised sub-sample of the event data such that the selected de-noised sub-sample of the event data does not represent flow cytometry events that satisfy a specified noise criterion,
wherein selecting, from the flow cytometry data, the sub-sample of the event data based on the sub-sampling ratio comprises selecting, from the de-noised sub-sample of the event data, the sub-sample of the event data based on the sub-sampling ratio.

8. The method of claim 1, wherein selecting, from the flow cytometry data, the sub-sample of the event data based on the sub-sampling rate comprises selecting data that corresponds to flow cytometry events selected according to a pre-determined pattern.

9. The method of claim 1, wherein the data sub-sampling ratio is a first data sub-sampling ratio, wherein the sub-sample of the event data is a first sub-sample of the event data, wherein the analysis is a first analysis, and wherein the method further comprises:
receiving a representation of the first analysis, wherein performing the first analysis on the first sub-sample of the event data and providing the indication of the result of the first analysis are performed responsive to receiving the representation of the first analysis, and wherein performing the first analysis on the first sub-sample of the event data comprises performing the first analysis according to the received representation of the first analysis;
receiving a representation of a second analysis;
selecting, from the flow cytometry data, a second sub-sample of the event data based on a second sub-sampling ratio such that the selected second sub-sample of the event data represents a portion of the flow cytometry events that corresponds to the second data sub-sampling ratio;
performing the second analysis on a second sub-sample of the event data according to the received representation of the second analysis; and
providing an indication of a result of the second analysis.

10. The method of claim 9, further comprising:
determining the second data sub-sampling ratio based on the performance criterion, wherein the performance criterion is an analysis duration criterion, and wherein determining the second data sub-sampling ratio based on the performance criterion comprises determining the second data sub-sampling ratio based on a number of the flow cytometry events in the flow cytometry data such that performing the second analysis on the second sub-sample of the event data can be performed in less than a specified duration of time.

11. A method for reducing flow cytometry data analysis computation time, the method comprising:
receiving, via a user interface, a data sub-sampling ratio;
receiving flow cytometry data, wherein the received flow cytometry data includes event data for a plurality of flow cytometry events;
selecting, from the flow cytometry data, a sub-sample of the event data based on the sub-sampling ratio such that the selected sub-sample of the event data represents a portion of the flow cytometry events that corresponds to the data sub-sampling ratio;
performing a reduced analysis on the sub-sample of the event data;
providing, via the user interface, an indication of a result of the reduced analysis;
receiving, via the user interface, an instruction to perform a full analysis;
responsive to receiving the instruction to perform the full analysis, performing the full analysis on the flow cytometry data; and
providing, via the user interface, an indication of a result of the full analysis.

12. The method of claim 11, wherein performing the full analysis additionally comprises applying a spectral compensation to the flow cytometry data, and wherein performing the reduced analysis does not include applying the spectral compensation to the flow cytometry data.

13. The method of claim 11, further comprising:
selecting, from the flow cytometry data, a de-noised sub-sample of the event data such that the selected de-noised sub-sample of the event data does not represent flow cytometry events that satisfy a specified noise criterion, wherein selecting, from the flow cytometry data, the sub-sample of the event data based on the sub-sampling ratio comprises selecting, from the de-noised sub-sample of the event data, the sub-sample of the event data based on the sub-sampling ratio, and wherein performing the full analysis on the flow cytometry data comprises performing the full analysis on the de-noised sub-sample of the event data.

14. A non-transitory computer-readable medium, configured to store at least computer-readable instructions that, when executed by one or more processors of a computing device, cause the computing device to perform controller operations comprising:

during a first period of time, receiving flow cytometry data, wherein the received flow cytometry data includes event data for a plurality of flow cytometry events;

determining a data sub-sampling ratio based on a performance criterion;

selecting, from the flow cytometry data, a sub-sample of the event data based on the sub-sampling ratio such that the selected sub-sample of the event data represents a portion of the flow cytometry events that corresponds to the data sub-sampling ratio;

performing an analysis on the sub-sample of the event data, wherein determining the data sub-sampling ratio comprises determining the data sub-sampling ratio such that performing the analysis on the sub-sample of the event data satisfies the performance criterion; and providing an indication of a result of the analysis.

15. The non-transitory computer-readable medium of claim 14, wherein performing the analysis and providing the indication of the result of the analysis are performed during the first period of time.

16. The non-transitory computer-readable medium of claim 15, wherein the performance criterion is a real-time latency criterion, and wherein determining the data sub-sampling ratio based on the performance criterion comprises determining the data sub-sampling ratio based on an average rate of occurrence of the flow cytometry events such that the analysis takes less time to perform than a duration of the first period of time.

17. The non-transitory computer-readable medium of claim 15, wherein performing the analysis on the sub-sample of the event data comprises updating the analysis a plurality of times during the first period of time as the flow cytometry data is received, and wherein providing the indication of the result of the analysis comprises providing an updated indication a plurality of times during the first period of time as the analysis is updated.

18. The non-transitory computer-readable medium of claim 14, wherein the performance criterion is an analysis duration criterion, and wherein determining the data sub-sampling ratio based on the performance criterion comprises determining the data sub-sampling ratio based on a number of the flow cytometry events in the flow cytometry data such that the analysis can be performed in less than a specified duration of time.

19. The non-transitory computer-readable medium of claim 18, wherein the analysis is characterized by a number of parameters, and wherein determining the data sub-sampling ratio further comprises determining an expected computation cost for the analysis based on the number of parameters.

20. The non-transitory computer-readable medium of claim 14, wherein the controller operations further comprise:

selecting, from the flow cytometry data, a de-noised sub-sample of the event data such that the selected de-noised sub-sample of the event data does not represent flow cytometry events that satisfy a specified noise criterion, wherein selecting, from the flow cytometry data, the sub-sample of the event data based on the sub-sampling ratio comprises selecting, from the de-noised sub-sample of the event data, the sub-sample of the event data based on the sub-sampling ratio.

21. The non-transitory computer-readable medium of claim 14, wherein selecting, from the flow cytometry data, the sub-sample of the event data based on the sub-sampling rate comprises selecting data that corresponds to flow cytometry events selected according to a pre-determined pattern.

22. The non-transitory computer-readable medium of claim 14, wherein the data sub-sampling ratio is a first data sub-sampling ratio, wherein the sub-sample of the event data is a first sub-sample of the event data, wherein the analysis is a first analysis, and wherein the controller operations further comprise:

receiving a representation of the first analysis, wherein performing the first analysis on the first sub-sample of the event data and providing the indication of the result of the first analysis are performed responsive to receiving the representation of the first analysis, and wherein performing the first analysis on the first sub-sample of the event data comprises performing the first analysis according to the received representation of the first analysis;

receiving a representation of a second analysis;

selecting, from the flow cytometry data, a second sub-sample of the event data based on a second sub-sampling ratio such that the selected second sub-sample of the event data represents a portion of the flow cytometry events that corresponds to the second data sub-sampling ratio;

performing the second analysis on a second sub-sample of the event data according to the received representation of the second analysis; and providing an indication of a result of the second analysis.

23. The non-transitory computer-readable medium of claim 22, wherein the controller operations further comprise:

determining the second data sub-sampling ratio based on the performance criterion, wherein the performance criterion is an analysis duration criterion, and wherein determining the second data sub-sampling ratio based on the performance criterion comprises determining the second data sub-sampling ratio based on a number of the flow cytometry events in the flow cytometry data such that performing the second analysis on the second sub-sample of the event data can be performed in less than a specified duration of time.

24. A non-transitory computer-readable medium, configured to store at least computer-readable instructions that, when executed by one or more processors of a computing device, cause the computing device to perform controller operations comprising:

receiving, via a user interface, a data sub-sampling ratio;

receiving flow cytometry data, wherein the received flow cytometry data includes event data for a plurality of flow cytometry events;

selecting, from the flow cytometry data, a sub-sample of the event data based on the sub-sampling ratio such that the selected sub-sample of the event data represents a portion of the flow cytometry events that corresponds to the data sub-sampling ratio;

performing a reduced analysis on the sub-sample of the event data;

providing, via the user interface, an indication of a result of the reduced analysis;

receiving, via the user interface, an instruction to perform a full analysis;

responsive to receiving the instruction to perform the full analysis, performing the full analysis on the flow cytometry data; and providing, via the user interface, an indication of a result of the full analysis.

25. The non-transitory computer-readable medium of claim 24, wherein performing the full analysis additionally comprises applying a spectral compensation to the flow cytometry data, and wherein performing the reduced analysis does not include applying the spectral compensation to the flow cytometry data.

26. The non-transitory computer-readable medium of claim 24, wherein the controller operations further comprise:

selecting, from the flow cytometry data, a de-noised sub-sample of the event data such that the selected de-noised sub-sample of the event data does not represent flow cytometry events that satisfy a specified noise criterion, wherein selecting, from the flow cytometry data, the sub-sample of the event data based on the sub-sampling ratio comprises selecting, from the de-noised sub-sample of the event data, the sub-sample of the event data based on the sub-sampling ratio, and wherein performing the full analysis on the flow cytometry data comprises performing the full analysis on the de-noised sub-sample of the event data.

* * * * *